US012702764B2

(12) United States Patent
Pedersen et al.

(10) Patent No.: US 12,702,764 B2
(45) Date of Patent: Aug. 11, 2026

(54) DRUG DELIVERY DEVICE ASSEMBLY AND ACCESSORY FOR DRUG DELIVERY DEVICE

(71) Applicant: AMGEN INC., Thousand Oaks, CA (US)

(72) Inventors: Jakob Halkjaer Pedersen, Frederiksberg (DK); Joshua Jay Dudman, Copenhagen (DK); Chiushun Dan, Thousand Oaks, CA (US); Kasper Friis, Horsholm (DK); Carsten Bech, Virum (DK); Adrianus Gerardus Verschuren, Newbury Park, CA (US); Michael John McColligan, Simi Valley, CA (US); Filip Saarman, Copenhagen (DK)

(73) Assignee: AMGEN INC., Thousand Oaks, CA (US)

( * ) Notice: Subject to any disclaimer, the term of this patent is extended or adjusted under 35 U.S.C. 154(b) by 603 days.

(21) Appl. No.: 18/032,759

(22) PCT Filed: Nov. 1, 2021

(86) PCT No.: PCT/US2021/057505
§ 371 (c)(1),
(2) Date: Apr. 19, 2023

(87) PCT Pub. No.: WO2022/098590
PCT Pub. Date: May 12, 2022

(65) Prior Publication Data

US 2023/0381426 A1 Nov. 30, 2023

Related U.S. Application Data

(60) Provisional application No. 63/217,679, filed on Jul. 1, 2021, provisional application No. 63/109,618, filed on Nov. 4, 2020.

(51) Int. Cl.
*A61M 5/42* (2006.01)
*A61M 5/20* (2006.01)
*A61M 5/32* (2006.01)

(52) U.S. Cl.
CPC .............. *A61M 5/427* (2013.01); *A61M 5/20* (2013.01); *A61M 5/3287* (2013.01)

(58) Field of Classification Search
CPC ........ A61M 2205/13; A61M 2205/583; A61M 2205/587; A61M 2209/088; A61M 5/42; A61M 5/427; A61M 5/3287; A61M 5/20
See application file for complete search history.

(56) References Cited

U.S. PATENT DOCUMENTS

2003/0229308 A1 12/2003 Tsals et al.
2010/0049126 A1 2/2010 Bronfeld et al.
(Continued)

FOREIGN PATENT DOCUMENTS

EP 3656425 A1 5/2020
JP 2017209427 A 11/2017
(Continued)

OTHER PUBLICATIONS

Japanese Patent Application No. 2023-526278, Notice of Reasons for Rejection, dated Jul. 1, 2025.
(Continued)

*Primary Examiner* — Deanna K Hall
(74) *Attorney, Agent, or Firm* — MARSHALL, GETSTEIN & BORUN LLP; Michael P. Furmanek

(57) ABSTRACT

A drug delivery device assembly is provided, including an injector housing, a needle assembly, a drive assembly, and an alignment accessory. The injector housing may include a body with a proximal end, a distal end, and a longitudinal axis extending between the proximal end and the distal end. The needle assembly is at least partially disposed within the
(Continued)

body and may include a syringe barrel containing a medicament and a needle or a cannula. The drive assembly is at least partially disposed within the body and operably coupled with the needle assembly to urge the medicament through the needle or cannula during an injection sequence. The needle or cannula is configured to pierce a patient's skin at an injection site. The alignment accessory includes an accessory body configured to be selectively coupled with the injector housing and an alignment aid configured to aid alignment of the accessory body with respect to the patient's skin at the injection site.

18 Claims, 19 Drawing Sheets

(56) References Cited

U.S. PATENT DOCUMENTS

2016/0235915 A1* 8/2016 Cabiri ................. A61M 5/3287
2021/0268188 A1* 9/2021 Katuin .............. A61M 5/31576

FOREIGN PATENT DOCUMENTS

WO WO-2020/072299 A1 4/2020
WO WO-2020/210142 A1 10/2020
WO WO-2020219672 A1 10/2020

OTHER PUBLICATIONS

International Search Report and Written Opinion for Application No. PCT/US2021/057505 dated Feb. 24, 2022.

* cited by examiner

DRUG DELIVERY DEVICE ASSEMBLY AND ACCESSORY FOR DRUG DELIVERY DEVICE

CROSS-REFERENCE TO RELATED APPLICATION

This is the United States national phase of International Patent Application No. PCT/US21/57505, filed Nov. 1, 2021, which claims priority to U.S. Provisional Patent Application No. 63/109,618, filed Nov. 4, 2020, and U.S. Provisional Patent Application No. 63/217,679, filed Jul. 1, 2021, the entire contents of each of which are hereby incorporated herein by reference.

FIELD OF THE INVENTION

This disclosure generally relates to a drug delivery device assembly and accessory for a drug delivery device. More particularly, the disclosure generally relates to an assembly with an alignment accessory and/or an alignment accessory that includes an accessory body configured to be selectively coupled with the injector housing and an alignment aid configured to maintain a desired alignment of the accessory body with respect to the patient's skin at the injection site.

BACKGROUND

Drugs are administered to treat a variety of conditions and diseases. Autoinjectors (e.g., pen style autoinjectors) and on-body injectors offer several benefits in delivery of medicaments such as drugs and/or therapeutics. One of the benefits can include simplicity of use, as compared with traditional methods of delivery using, for example, conventional syringes. Autoinjectors may be used to deliver many different medicaments with varying viscosities and/or desired volumes.

It may be desirable for autoinjector users to maintain a particular force level and/or orientation during the injection. Autoinjector IFUs may instruct, encourage, or recommend such actions. For example, a user may desire to or be instructed to maintain a constant or baseline force and/or to maintain the autoinjector in an orientation perpendicular to the injection site during the injection sequence. These steps may increase the likelihood of a complete and successful injection and/or reduce pain or discomfort.

It may also be desirable for autoinjector users to inspect and/or observe certain characteristics of the autoinjector before and/or during use. Autoinjector instructions for use ("IFU") may instruct, encourage, or recommend such inspection actions. For example, a user may desire to or be instructed to inspect a medicament via an autoinjector viewing window before using an autoinjector, such as to check for particulates, discoloration, or contaminants. A user may desire to or be instructed to observe the viewing window during the injection process, or at least before removing the autoinjector from contact with the patient's skin. More specifically, during the injection sequence the user may observe the decreasing volume of the medicament and the plunger stopper urging the medicament from the drug delivery device to determine when the injection is complete. These steps may reduce the likelihood of premature removal of the device from the delivery site, which can result in an incomplete dosage being delivered due to the drug spraying onto the skin surface.

However, some autoinjector users may find it awkward, uncomfortable, or otherwise inconvenient to apply the desired force at the desired orientation, for example while also observing the viewing window.

As described in more detail below, the present disclosure sets forth a drug delivery device assembly and an accessory for drug delivery devices, such as autoinjectors, that embodies advantageous alternatives to existing systems and methods, and that may address one or more of the challenges or needs mentioned herein, as well as provide other benefits and advantages.

SUMMARY

A drug delivery device assembly is provided, including an injector housing, a needle assembly, a drive assembly, and an alignment accessory. The injector housing may include a body with a proximal end, a distal end, and a longitudinal axis extending between the proximal end and the distal end. The needle assembly is at least partially disposed within the body and may include a syringe barrel containing a medicament and a needle or a cannula. The drive assembly is at least partially disposed within the body and operably coupled with the needle assembly to urge the medicament through the needle or cannula during an injection sequence. The needle or cannula is configured to pierce a patient's skin at an injection site. The alignment accessory includes an accessory body configured to be selectively coupled with the injector housing and an alignment aid configured to aid alignment of the accessory body with respect to the patient's skin at the injection site.

The alignment aid may be configured to aid alignment of the accessory body with respect to the patient's skin at the injection site by conveying to a user information regarding a position of the accessory body with respect to the patient's skin at the injection site. Additionally or alternatively, the alignment aid may be configured to aid alignment of the accessory body with respect to the patient's skin at the injection site by maintaining a position of the accessory body with respect to the patient's skin at the injection site.

The alignment aid may include first sensor, which may be a contact sensor, configured to detect a position of the accessory body with respect to the patient's skin at the injection site. The alignment aid may include second, third, and fourth sensors, which may each be contact sensors. The four sensors may be generally equally spaced around a circular path along the accessory body. The alignment accessory may include four indicator lights respectively, operatively coupled with the four sensors.

The alignment aid may include a contoured portion configured to generally fit the contour of a patient's injection site. The alignment aid may also include a securing portion configured to selectively secure the alignment accessory with the patient. The securing portion may be an adjustable strap.

The alignment aid may include a securing portion, which may include an adhesive, configured to selectively secure the alignment accessory with the patient. The accessory body may be a ring portion configured to receive a portion of the injector housing.

An alignment accessory for a drug delivery device is also provided, including an accessory body configured to be selectively coupled with an injector, and an alignment aid configured to aid alignment of the accessory body with respect to a patient's skin at an injection site.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description.

DETAILED DESCRIPTION

Generally speaking, pursuant to these various embodiments, a drug delivery device (e.g., an autoinjector or other injector) is coupled with or used in conjunction with an accessory to aid with alignment. For example, the accessory may be coupled with the injector and configured to aid alignment of the accessory body with respect to the patient's skin at the injection site.

The term "about" as used herein means +/−10% to the smallest significant digit. The term "patient's skin" may refer to the users uncovered, naked, or bare skin and/or the user's skin as it is covered by clothing, bandage, or other covering.

Figure 1:
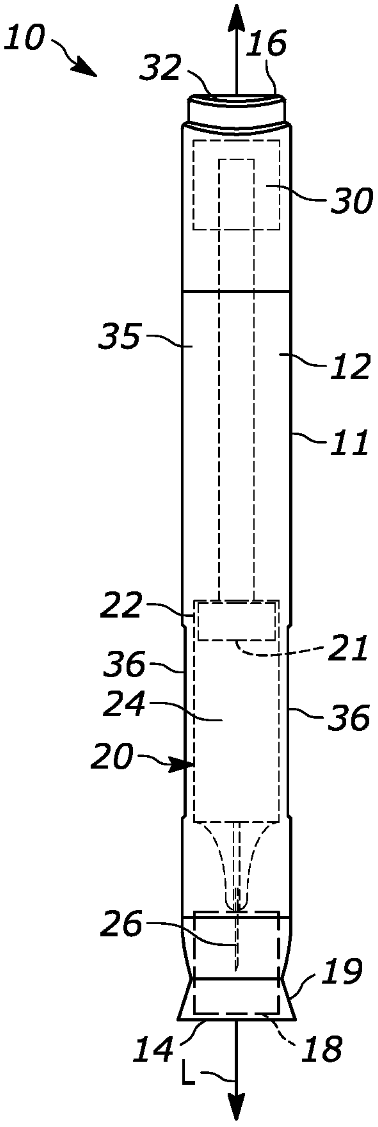
FIG. 1 is a front view of an exemplary drug delivery device that may be utilized with aspects of the present disclosure.

As illustrated in FIG. 1, an example injector 10 generally includes an injector housing 11 defining a housing 12 that includes a distal end 14, a proximal end 16, and a longitudinal axis L extending between the distal and proximal ends 14, 16. The injector 10 distal end 14 includes a generally cylindrical shaped needle shield 18 that assists with actuation of the injector 10 and a needle cap 19 that covers the needle shield 18 prior to use of the injector. A needle assembly 20 is at least partially disposed within the housing 12 at or near the distal end 14, and includes a syringe barrel 22 that contains a medicament 24, a plunger stopper 21 disposed within the syringe barrel 22, and a needle or a cannula 26 that is used to inject the medicament 24 into a patient at a desired injection site. In the illustrated example, the needle or cannula 26 is initially positioned within the housing 12 prior to activation, and may protrude through an opening in the distal end 14 during drug delivery.

A drive assembly 30 is also at least partially disposed within the housing 12 and is operably coupled to the needle assembly 20. The drive assembly 30 may include an actuator button 32 positioned at or near the proximal end 16 of the housing 12 that initiates actuation of the drive assembly 30. In operation, a user removes the needle cap 19, places the needle shield 18 against the injection location (e.g., on their leg or their stomach), and actuates the actuator button 32. This actuation causes a drive mechanism (in the form of a spring, a motor, a hydraulic or pressurized mechanism, etc.)

of the drive assembly 30 to exert a driving force on a portion of the needle assembly 20, such as the plunger stopper 21, that causes the needle or cannula 26 to be inserted through the opening of the housing 12 and into a patient and/or that further causes the medicament 24 to be urged from the syringe barrel 22, out the needle or cannula 26, and into the patient. In some versions, the patient may manually insert the needle or cannula 26, and actuation of the drive mechanism 30 only includes urging the plunger stopper 21 in the distal direction thereby causing the medicament 24 to be urged from the syringe barrel 22, out the needle or cannula 26, and to the patient. The injector 10 may not include an actuator button and may instead be activated by movement of the needle shield 18 alone, rather than an actuator button plus movement of the needle shield.

The injector 10 may include any number of additional features and components that may assist and/or enhance the functionality of the device. In the illustrated example, a viewing window 36 positioned at or near the syringe barrel 22 provides a visual indication of the remaining quantity of drug during administration. The needle cap 19 shields the needle 26 and prevents unintentional activation of the injector 10 and deployment of the needle or cannula 26. The needle shield 18 acts to unlock or initiate the injection when the needle shield 18 is pressed against a patient's skin. The activation of the drive assembly 30 requires a specific force to be applied to the needle shield 18 of the injector 10 and that force is transferred to the user's skin. In other examples, the injector 10 may additionally include one or more electronic modules that are coupled to the housing 12, the needle assembly 20, the drive assembly 30, and/or any other components of the injector 10. Further, the injector 10 may also include any number of safety mechanisms such as a retraction mechanism, damping mechanism, and the like.

The present example of the drug delivery device 10 takes the form of an autoinjector or pen-type injector, and, as such, may be held in the hand of the user over the duration of drug delivery. The drug delivery device 10 may be suitable for self-administration by a patient or for administration by caregiver or a formally trained healthcare provider (e.g., a doctor or nurse). However, various implementations and configurations of the drug delivery device 10 are possible. In other examples, the drug delivery device 10 may be configured as a multiple-use reusable injector.

Figure 2A:
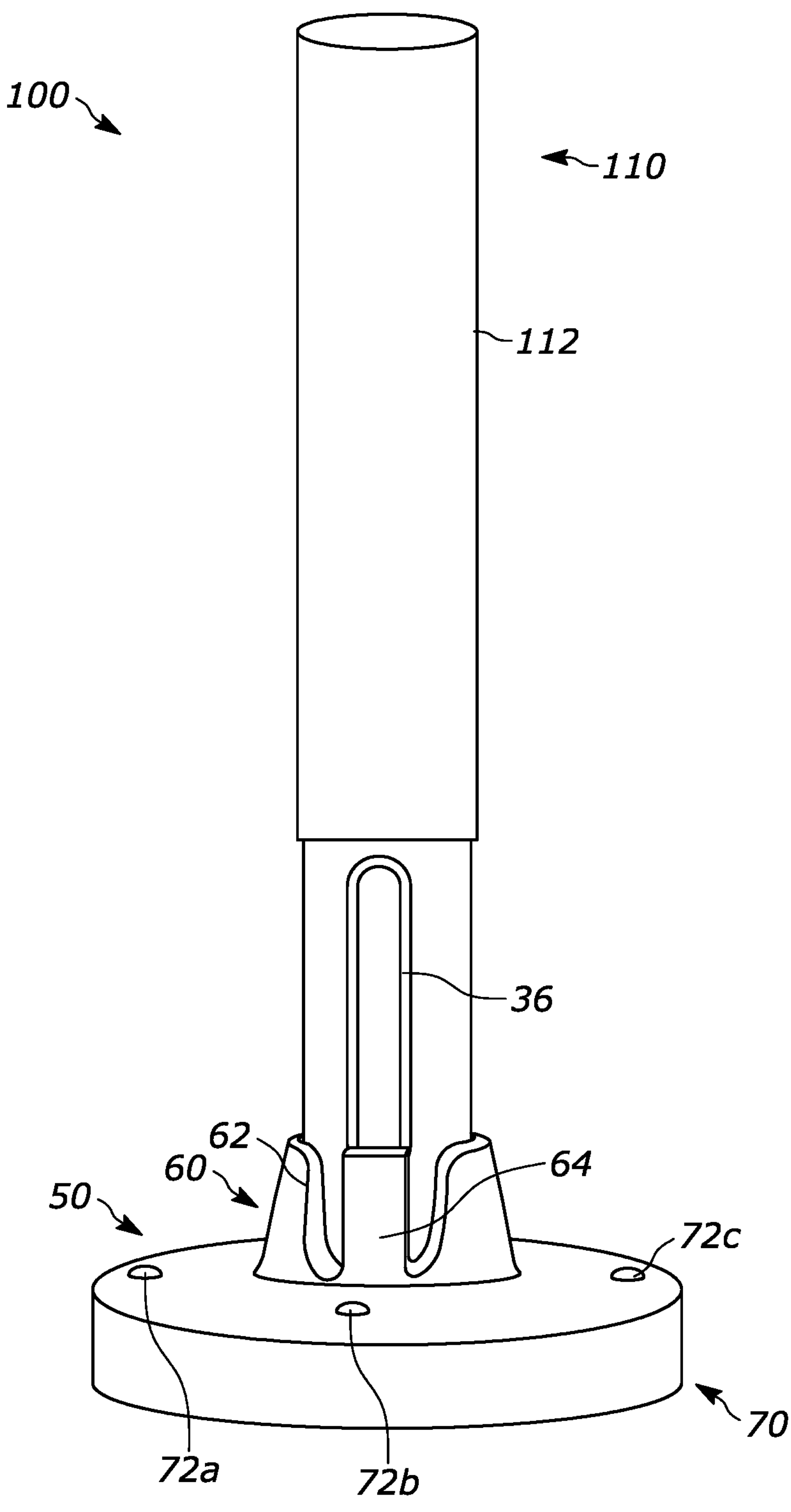
FIG. 2A is a front view of an exemplary drug delivery device assembly according to aspects of the present disclosure, including an injector and an accessory having an alignment aid.

FIG. 2A shows a drug delivery device assembly 100, including an injector 110 and an accessory 50 according to aspects of the present disclosure. The accessory 50 includes an accessory body 60 configured to be selectively coupled with the injector housing 112, an alignment aid 70 configured to aid alignment of the accessory body 60 with respect to the patient's skin at the injection site.

Figure 2B:
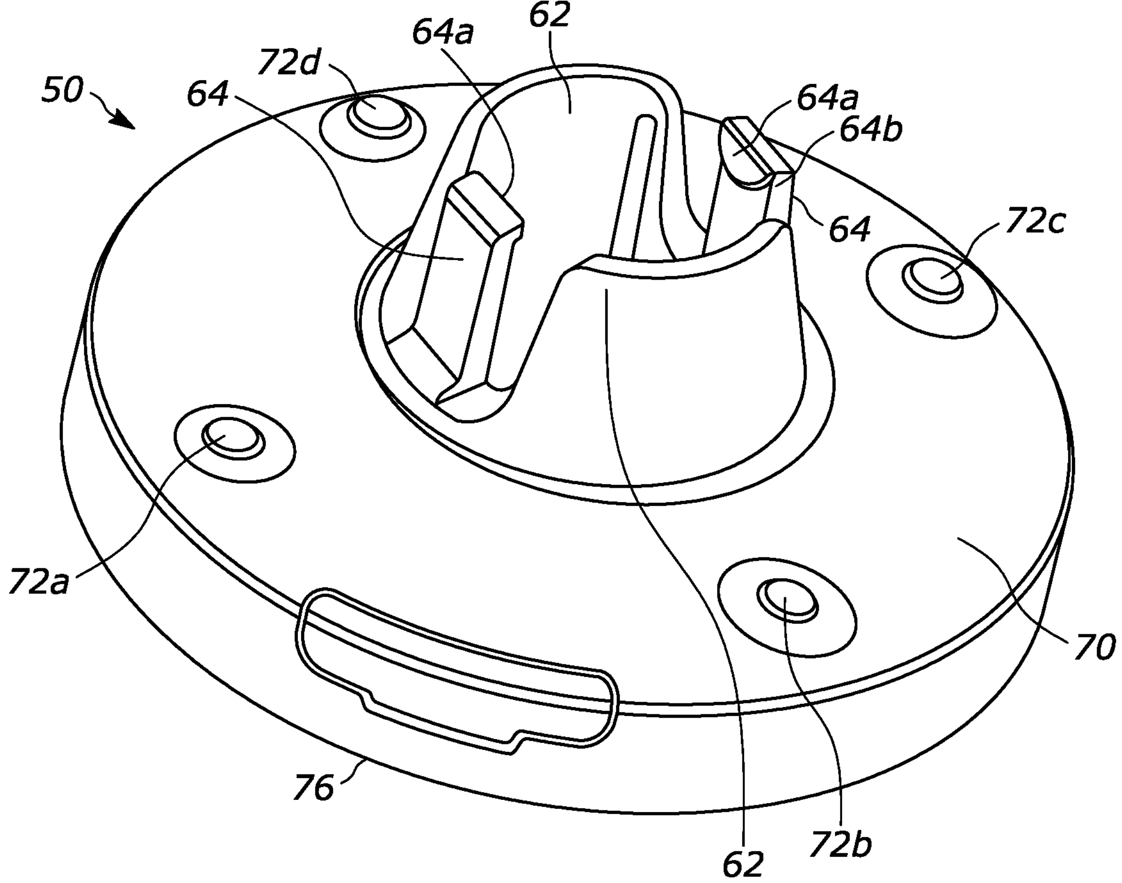
FIG. 2B is a top side perspective view of the alignment aid shown in FIG. 2A.

The accessory body 60 may include two opposing support flanges 62, each having an inner surface that generally aligns with and is able to receive a portion of the injector housing 112. The flanges 62 may generally extend in a direction parallel with the longitudinal axis L of the injector and/or generally perpendicular to a bottom surface of the accessory 50, as will be discussed in more detail below. The accessory body 60 may also include two opposing locking arms 64 that selectively lock the accessory 50 with the injector 110. For example, the locking arms 64 may lock, couple, or otherwise holds together the accessory 50 and the injector 110. As a more specific example, the locking arms 64 may have ridges **64*a* that are able to be received within and/or against a surface of the accessory body 60 and the locking arms 64 may be able to flex radially outward while the injector 110 is being slid into the accessory body 60 and to move radially inward when the injector 110 is in its fully-inserted position. In other words, the locking arms 64 are able to flex outward and then snap inward. As mentioned above, the ridges may abut a surface of the accessory body 60 to selectively lock the accessory body 60 and the injector. For example, when in a locked position (as shown in FIG. 2A), the ridges 64*a* may abut the lower (e.g., distal) surface of the window 36 to prevent the injector 110 from moving proximally with respect to the accessory 50 while the locking arms 64 are in the locked position. The locking arms 64 may be released in various ways, such as the user manually bending (e.g. flexing) the locking arms 64 radially outward. As another example, the locking arms 64 may be released by the user rotating the injector 110 with respect to the accessory 50 such that the ridges 64*a* rotate out of the windows 36. In such a configuration, the ridges 64*a* may have sloped surface or rounded edges 64*b* (FIG. 2B) to facilitate unlocking of the locking arms 64 with respect to the injector 110. In other words, the edges 64*b* of the locking arms 64 may operate as a type of camming mechanism such that as the injector 110 is rotated with respect to the accessory 50 (or vice versa), the locking arms 64 move simultaneously in a rotational direction and a radially outward direction, thereby causing the locking arms 64 to no longer sit within the window 36 and to no longer lock the accessory 50 with respect to the injector 110**.

Figure 2C:
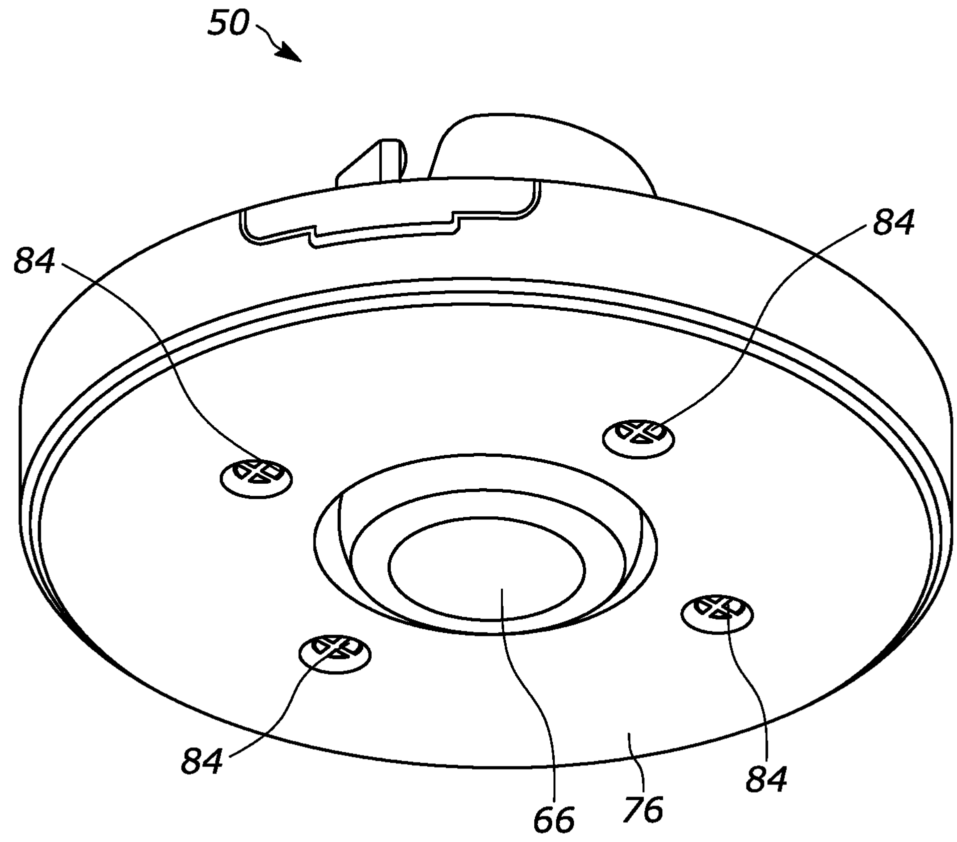
FIG. 2C is a bottom side perspective view of the alignment aid shown in FIG. 2A.

As shown in FIG. 2C, the accessory body 60 further includes a cylindrical opening 66 distally located of the support flanges 62 and locking arms 64. The cylindrical opening 66 may receive the distal portion of the injector housing 112, such as the portion of the injector 110 adjacent to the needle shield 18. The cylindrical opening 66 may have a diameter and shape so as to form a friction fit with the injector 110. In such an embodiment, the locking arms 64 may not be necessary and the injector 110 may be removed from engagement with the accessory 50 by pulling and/or rotating the injector 110 with respect to the accessory 50.

As mentioned above, the accessory 50 includes an alignment aid 70 configured to aid alignment of the accessory body 60 with respect to the patient's skin at the injection site. The alignment aid 70 shown in FIGS. 2A-2F includes at least two main features to aid alignment of the accessory body 60 with respect to the patient's skin at the injection site, namely: a relatively wide contact surface 76 for engaging the injection site and alignment sensors 74 and alignment indicators 72 to alert the user when the assembly 100 is properly aligned with the injection site. Both of these main features are described below in more detail.

The relatively wide contact surface 76 provides the user with a wider surface (i.e., wider than the distal portion of the injector 100) for contacting the user's skin, such that the contact forces acting on the users skin may be more spread out, the users skin may be less likely to buckle or fold during contact, and/or it may be easier for the user to hold the drug delivery device in the desired orientation (perpendicular to the injection site). As a more specific example, the diameter of the contact surface 76 is approximately 4 to 5 times larger than the diameter of the injector 110. Alternatively, the diameter of the contact surface may be any suitable size, such as 1.5 to 2 times larger than the diameter of the injector, 2 to 3 times larger than the diameter of the injector, 3 to 4 times larger than the diameter of the injector, 4 to 5 times larger than the diameter of the injector, 5 to 6 times larger than the diameter of the injector, or any other suitable size. The size of the contact surface 76 may also serve another function, such as helping the user properly align the injector in a direction such that the needle is generally perpendicular to the patient's skin at the injection site. As a more specific example, some users may find it easier to align a larger contact surface (e.g., the contact surface 76) with the injection site because it is easier to see and/or feel when the contact surface 76 is parallel with and/or pressed flat against the skin. As another example, the contact surface 76 may also flatten the users skin at the injection site, thereby causing a more predictable and/or repeatable injection experience.

Figure 2D:
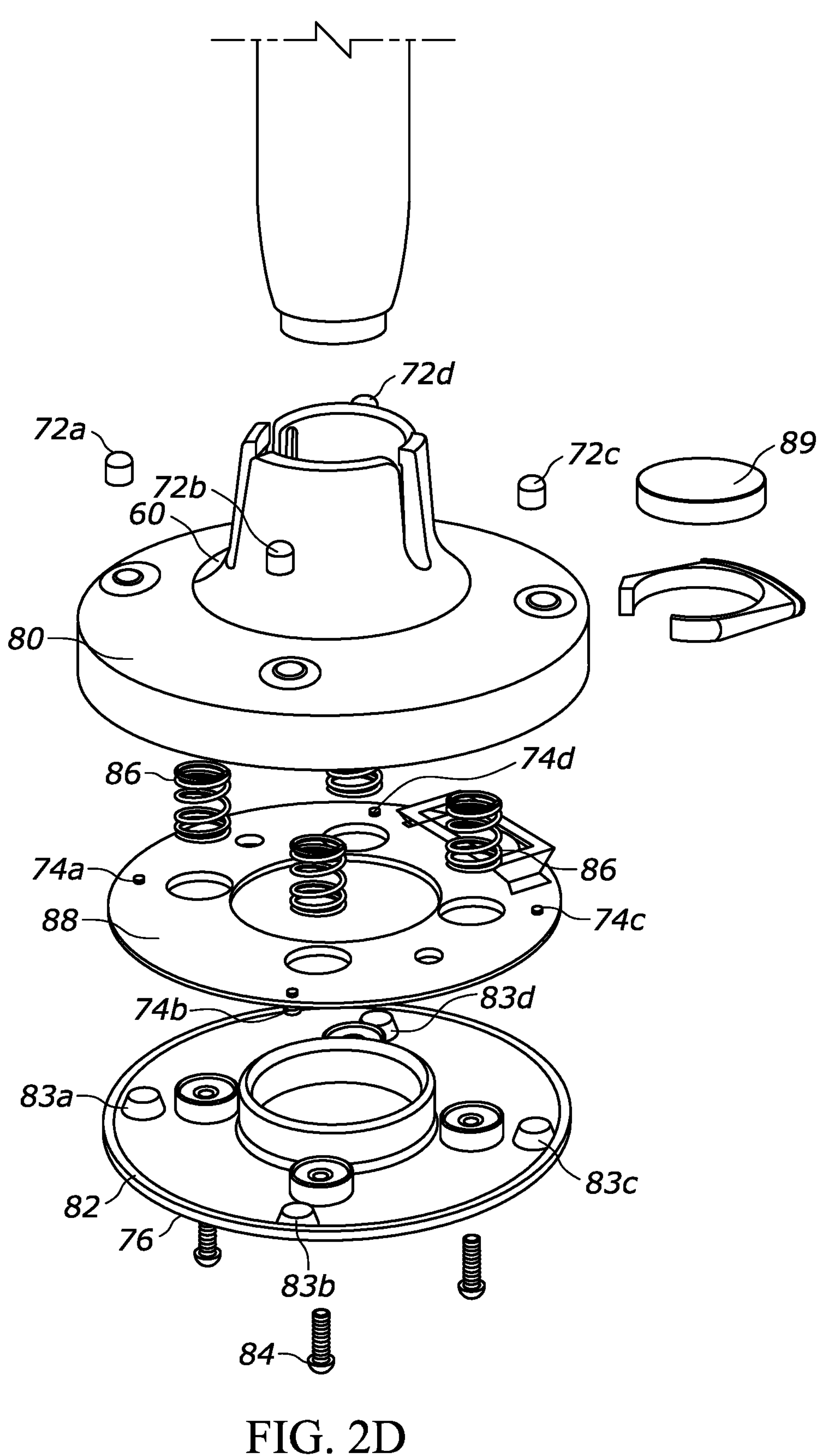
FIG. 2D is an exploded view of the alignment aid shown in FIG. 2A.
Figure 2E:
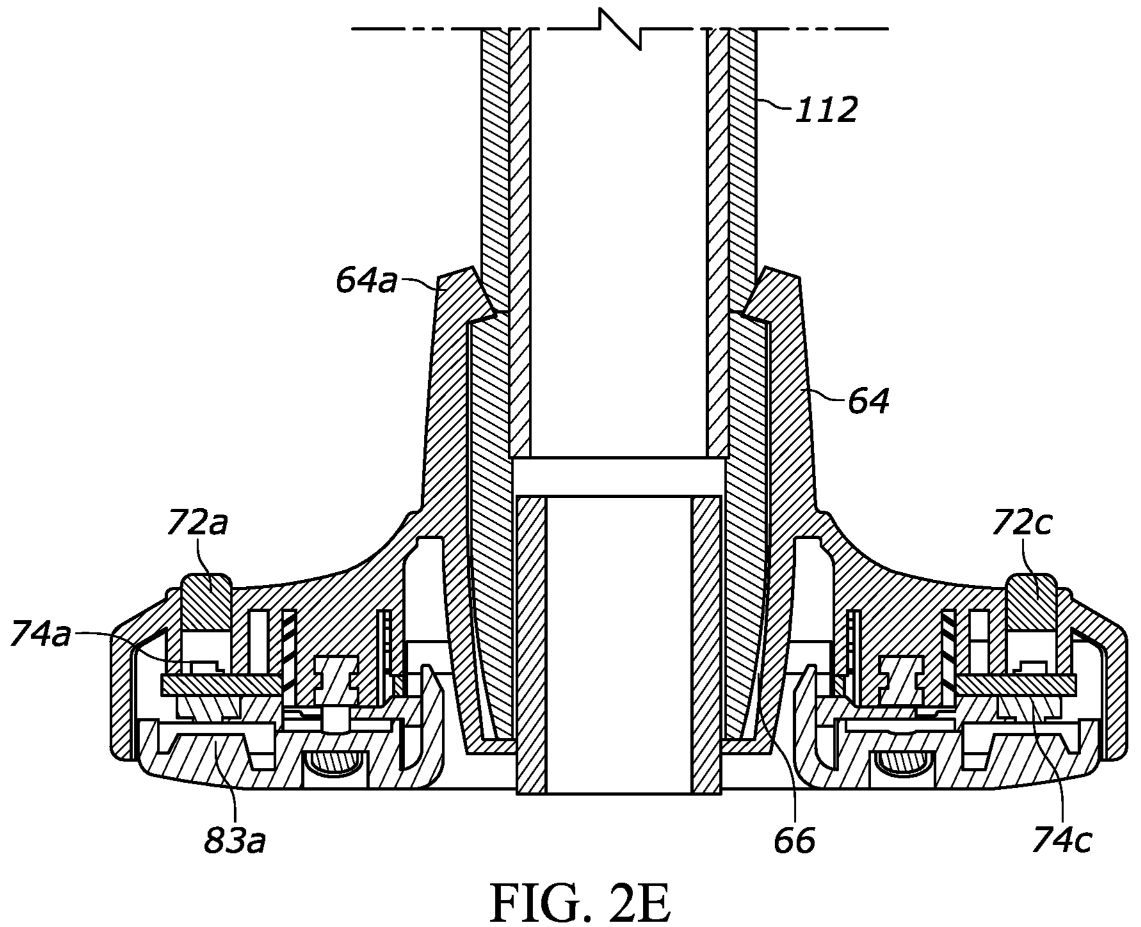
FIG. 2E is a cross-sectional view of the alignment aid shown in FIG. 2A.

As mentioned above, the second main feature to help with alignment is at least one alignment sensor 74 and at least one alignment indicator 72. As a more specific example, the accessory shown in FIGS. 2A-2F includes four alignment sensors 74*a*, 74*b*, 74*c*, 74*d* and four corresponding alignment indicators 72*a*, 72*b*, 72*c*, 72*d*. The alignment sensors 74*a*, 74*b*, 74*c*, 74*d* may be mechanical sensors that have a moving component that will be depressed or otherwise moved when the accessory 50 contacts the user's skin. As a more specific example, and as best shown in FIGS. 2D-2E, the accessory 50 includes an upper housing 80 that defines the accessory body 60, a lower housing 82 that defines the contact surface 76 and is coupled with the upper housing 80 via fasteners 84, a plurality of springs 86 positioned between the upper 80 and lower housing 82 to bias the respective components 80, 82 away from each other and create a "floating relationship" therebetween, a circuit board 88 and battery 89 operably coupled with the switches 74 and the indicators 72, the four mechanical switches 74*a*, 74*b*, 74*c*, 74*d*, and the four corresponding alignment indicators 72*a*, 72*b*, 72*c*, 72*d*. The upper housing 80 and lower housing 82 are coupled with each other such that the lower housing 82 "floats" with respect to the upper housing 80. In other words, the lower housing 82 is able to move inward (in the proximal direction) within the upper housing 80 at a variety of angles. As an even more specific example, the four springs 86 outwardly bias the lower housing 82 away from the upper housing 80, but the lower housing 82 is also able to be depressed inward into the upper housing 80 upon an external force such as a user depressing the accessory 50 against the users skin. The two-piece housing "floating" design further refers to the fact that the lower housing 82 is able to move such that it is not parallel with the upper housing 80. In other words, the lower housing 82 can be tilted or angled with respect to the upper housing 80 when the force applied by the user is not perpendicular to the skin surface at the injection site. As a more specific example, the lower housing 82 openings that receive the fasteners 84 are large enough such that the lower housing 82 is able to tilt with respect to the fasteners 84 and with respect to the upper housing 80.

The lower housing 82 also includes four protrusions 83*a*, 83*b*, 83*c*, 83*d* that are each aligned with four mechanical switches 74*a*, 74*b*, 74*c*, 74*d*. When the lower housing 82 is fully extended (e.g., during its resting state) the four protrusions 83*a*, 83*b*, 83*c*, 83*d* do not engage the four mechanical switches 74*a*, 74*b*, 74*c*, 74*d*. When the lower housing 82 is fully depressed (e.g., when a user is depressing the injector and/or the accessory flat against the users skin with sufficient force) then each of the four protrusions 83*a*, 83*b*, 83*c*, 83*d* will respectively contact its corresponding mechanical switch 74*a*, 74*b*, 74*c*, 74*d*. When the lower housing is partially depressed (e.g., when a user is depressing the injector at a non-perpendicular angle or without sufficient force) then only some or none of the protrusions will contact switches.

When one of the protrusions 83*a*, 83*b*, 83*c*, 83*d* contacts its mechanical switch 74*a*, 74*b*, 74*c*, 74*d*, then the corresponding alignment indicator 72*a*, 72*b*, 72*c*, 72*d* lights up. As a result, a user is observe the alignment indicators 72*a*, 72*b*, 72*c*, 72*d* and determine which portion(s) of the bottom housing 82 have been sufficiently depressed. In other words, the user may be able to adjust force and orientation of the injector 110 until all four alignment indicators 72*a*, 72*b*, 72*c*, 72*d* are lit. Once all four alignment indicator 72*a*, 72*b*, 72*c*, 72*d* are lit, the user can proceed with the injection.

The indicators shown in the figures may be light-emitting diode (LED) lights, organic light-emitting diode (OLED) lights, incandescent lights, neon lights, or any other suitable type of lights.

Figure 2F:
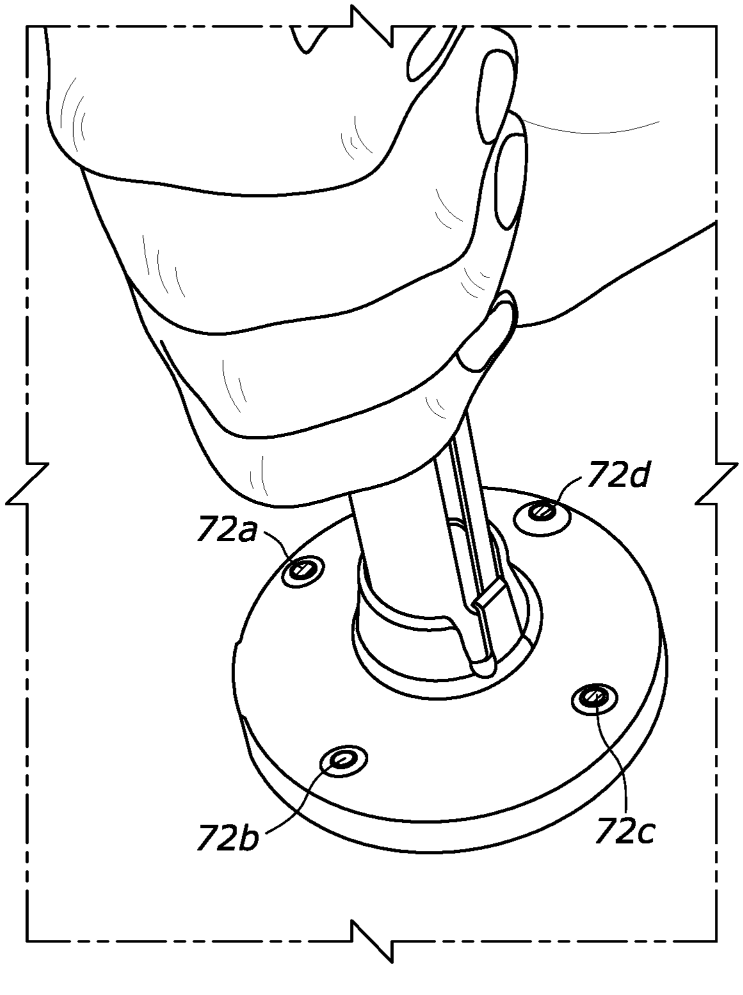
FIG. 2F is a top side perspective view of the assembly in FIG. 2A, wherein three of the four alignment aid indicators are lit up.

FIG. 2F shows the system in use. For example, the indicator lights 72*a*, 72*c*, and 72*d* are lit up, thereby indicating to the user that those three sections of the lower housing 82 are sufficiently depressed to depress mechanical switches 74*a*, 74*c*, and 74*d*. However, the user will also be able to determine that the injector is not completely aligned based on the fact that indicator light 72*b* is not lit. As a result, the user will know to angle the injector slightly towards indicator light 72*d* until all four indicator lights are lit up.

In an alternate configuration, the sensors may a different type of sensor, other than a mechanical switch. As a more specific example, each of the alignment sensors detects contact, light, and/or other measurable or detectable conditions to determine whether the discrete portion of the contact surface 76 nearby each alignment sensor is properly engaged with and/or aligned with the user's skin. For example, the alignment sensors in such an embodiment may be light sensors that are able to detect and/or measure the amount of light exposed to each sensor location. When a portion of the contact surface is pressed up against and/or adjacent to the users skin, then the sensor that is close to that portion of the contact surface likely will be covered by the user's skin such that little or no light is able to reach the sensor. When most or all of the contact surface is in contact with the users skin (i.e., properly aligned) then all four sensors will be covered. Each of the alignment sensors is operatively coupled with four alignment indicators such that the alignment indicators are able to convey to a user when the sensors are covered. Therefore, when all four alignment indicators are lit up, then the user will know that all four sensors are covered and the injector is properly aligned.

The alignment indicators 72*a*, 72*b*, 72*c*, 72*d* may also have other configurations, such as lights that turn off (instead of turn on) when the contact surface is aligned. Alternatively, the indicators may not be light-based and may instead be tactile, auditory, or other types of indicators.

FIGS. 3A-3E shows a drug delivery device assembly 200, including an injector 210 and an accessory 250 according to aspects of the present disclosure. The accessory 250 includes an accessory body 260 configured to be selectively coupled with the injector housing 212, an alignment aid 270 configured to aid alignment of the accessory body 260 with respect to the patient's skin at the injection site.

The accessory body 260 may include a generally cylindrical sleeve 262 defining a generally cylindrical opening 264 configured to receive a portion of the injector housing 212. The sleeve may also have receiving slots 263 for receiving locking knobs 234 on the autoinjector 210. The sleeve 260 may further include locking slots 265 that are perpendicular to the receiving slots 263 that may allow a user to rotate the injector 200 to cause the injector locking knobs 234 to move along the locking slots 265 and then prevent longitudinal movement of the injector housing 212 with respect to the accessory 250. The injector locking knobs 234 may also prevent the injector from rolling when disconnected from the accessory).

As mentioned above, the accessory 250 includes an alignment aid 270 configured to aid alignment of the accessory body 260 with respect to the patient's skin at the injection site. For example, the accessory 250 shown in FIGS. 3A-3E includes at least two main features to aid alignment of the accessory body 260 with respect to the patient's skin at the injection site, namely: a contoured portion 272 configured to generally fit the contour of a patient's skin at the injection site and a securing portion 274 configured to selectively secure the accessory 250 with the patient.

The contoured portion 272 has a generally arcuate shape to conform to a portion of a curved section of a patient's body, such as the patient's thigh. The contoured portion 272 may be flexible to conform to different shapes of different patients and different body parts or it may be relatively rigid and available in different shapes and sizes. The contoured portion may have a relatively wide contact surface 276 that contacts the user's skin adjacent to the intended injection. The relatively wide contact surface 276 may provide the user with a wider surface (i.e., wider than the distal portion of the injector 200) for contacting the users skin, such that the contact forces acting on the users skin may be more spread out, the user's skin may be less likely to buckle or fold during contact, and/or it may be easier for the user to hold the drug delivery device in the desired orientation (perpendicular to the injection site). As a more specific example, the length and width of the contact surface 276 are each approximately 3 to 5 times larger than the diameter of the injector 210. Alternatively, the length and width of the contact surface 276 are each approximately 2 to 6 times larger than the diameter of the injector, 2 to 8 times larger than the diameter of the injector, 2 to 10 times larger than the diameter of the injector, or any other suitable size. The size of the contact surface 276 may also serve another function, such as helping the user properly align the injector in a direction such that the needle is generally perpendicular to the patient's skin at the injection site. As a more specific example, some users may find it easier to align a larger contact surface (e.g., the contact surface 276) with the injection site because it is easier to see and/or feel when the contact surface 276 is parallel with and/or pressed flat against the skin. As another example, the contact surface 276 may also make the skin a more evenly contoured shape in the area of the injection site, thereby causing a more predictable and/or repeatable injection experience.

The securing portion 274 is coupled to opposite ends of the contoured portion 272 and configured to selectively secure the accessory 250 with the patient. As a more specific example, the securing portion 274 is a strap configured to selectively secure the contoured portion 272 to the patient's body 280, such as by wrapping around a portion of the patient's skin 282, such as the patient's thigh. The securing portion may be an adjustable strap that has a variable (adjustable) length, a flexible strap, and/or any other suitable configuration. The strap 274 shown in FIGS. 3A-3E has one end 275 that forms a closed loop around one end of the contoured portion, a second end 277 that is a straight section (not a closed loop) that is able to be threaded through a portion of the contoured portion 272 and then fold back to secure to itself, such as by Velcro fasteners.

Figure 3A:
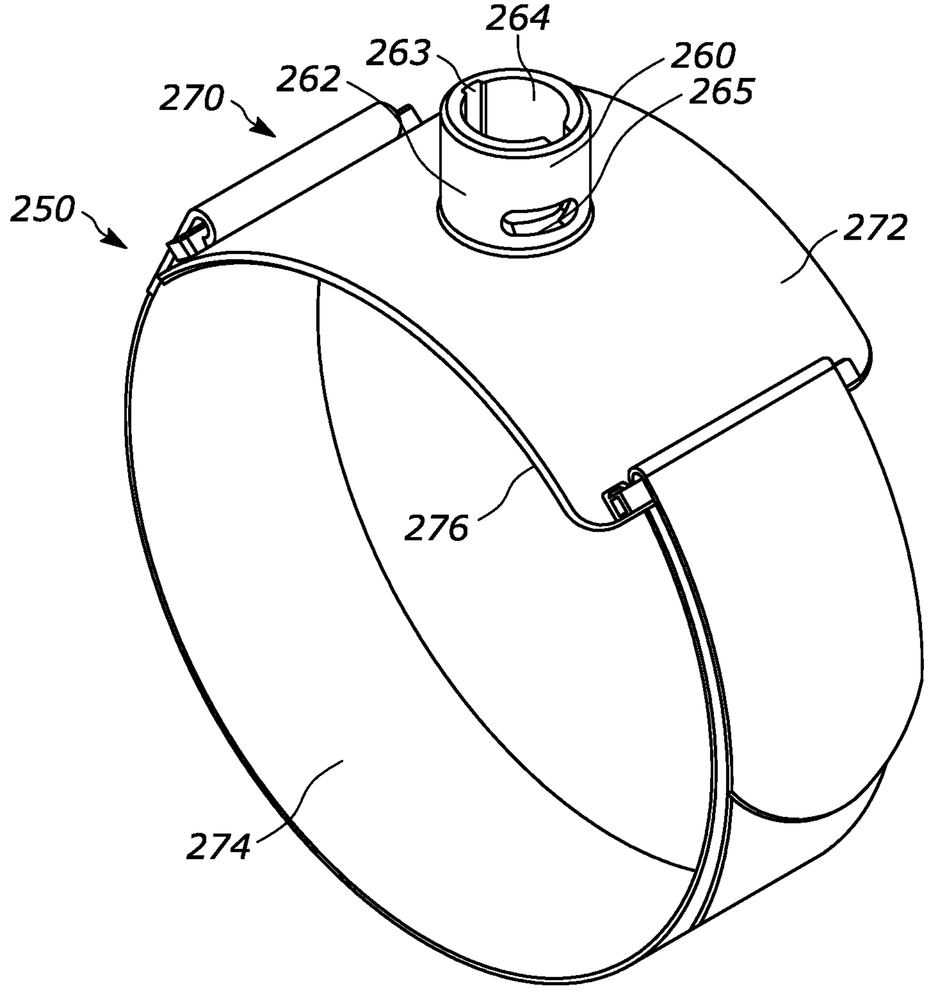
FIG. 3A is a perspective view of an accessory having an alignment aid for a drug delivery device according to aspects of the present disclosure.
Figure 3B:
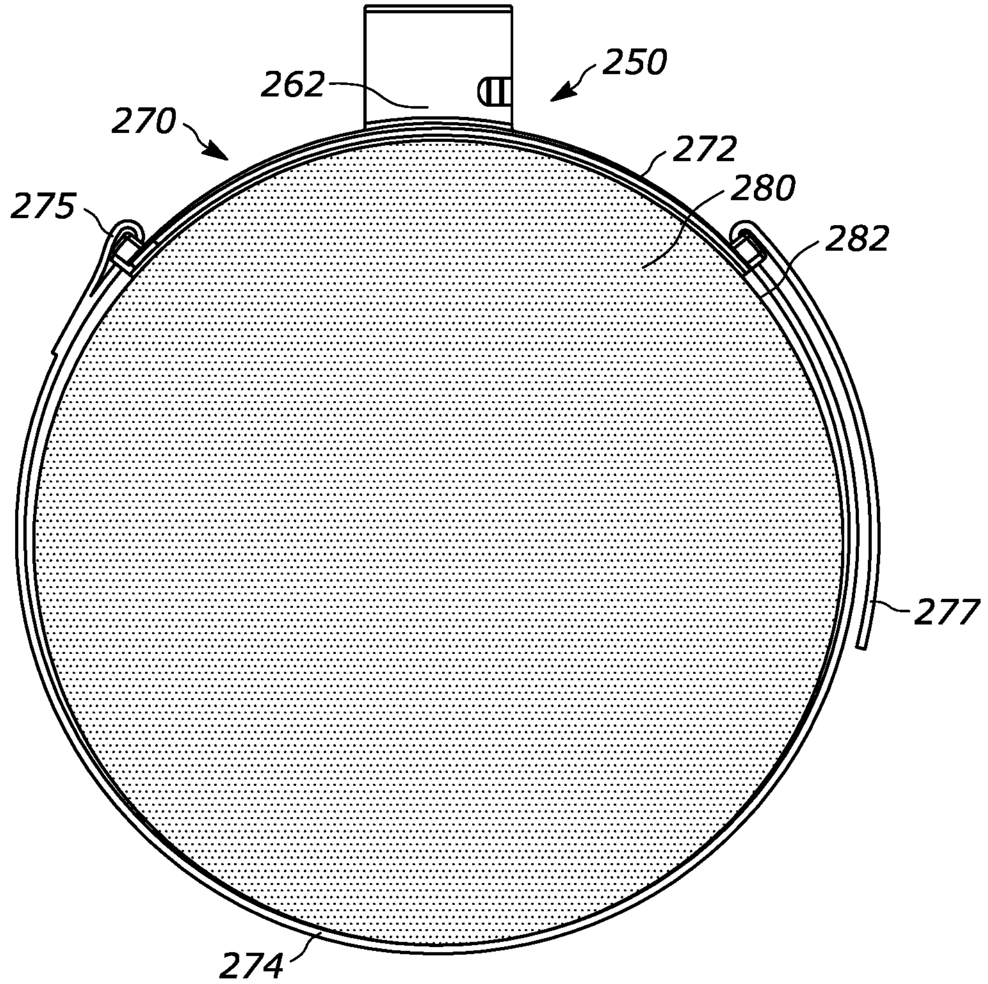
FIG. 3B is a cross-sectional view of a portion of a patient's body coupled with the alignment aid shown in FIG. 3A.
Figure 3C:
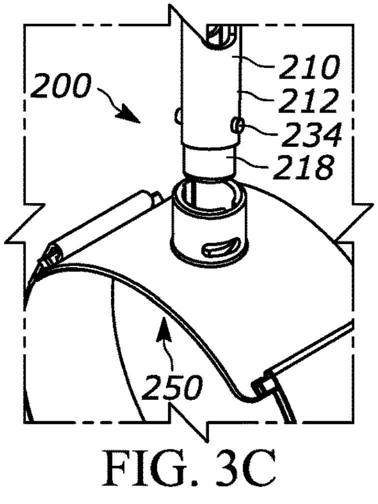
FIG. 3C shows an injector before coupled with accessory shown in FIG. 3B.
Figure 3D:
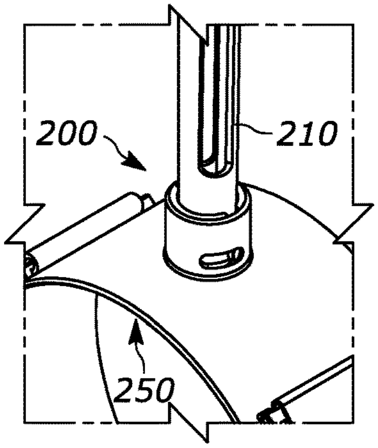
FIG. 3D shows the assembly from FIG. 3B once the injector has been fully inserted but not locked.
Figure 3E:
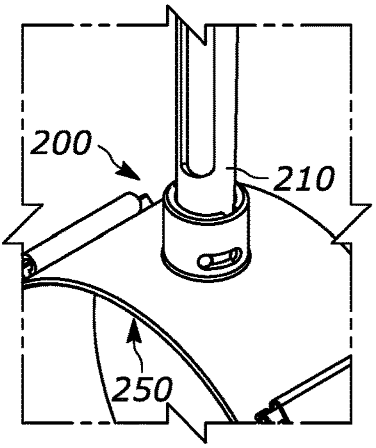
FIG. 3E shows the assembly from FIG. 3B once the injector has been locked (via rotation) with the accessory.

FIGS. 3C-3E show the injector 210 during stages of coupling with the accessory 250. FIG. 3C shows accessory 250 once it has been coupled with the patient such that the collar portion is aligned with the desired injection site, but before the injector 210 has been inserted into the body 260. FIG. 3D shows the assembly 200 once the injector 210 has been fully inserted but not locked. The longitudinal movement of the injector 210 may depress the needle shield 218 and may trigger the injection sequence. FIG. 3E shows the assembly 200 once the injector 210 has been locked (via rotation) with the accessory 250 so the user is able to release/let go of the injector without necessarily affecting the injection efficacy and/or repeatability.

Figure 4A:
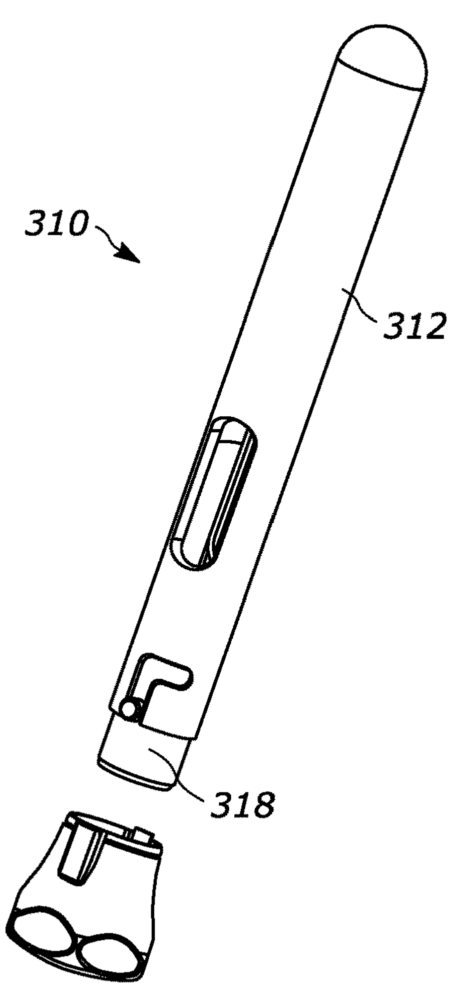
FIG. 4A shows an injector according to aspects of the present disclosure.
Figure 4B:
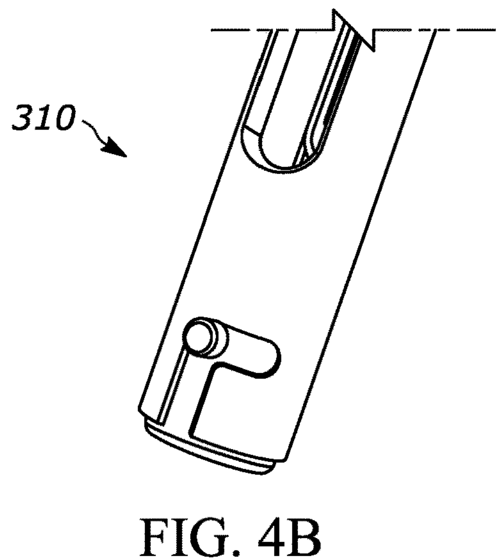
FIG. 4B shows the injector from FIG. 4A, where the needle shield has been depressed but not rotated.
Figure 4C:
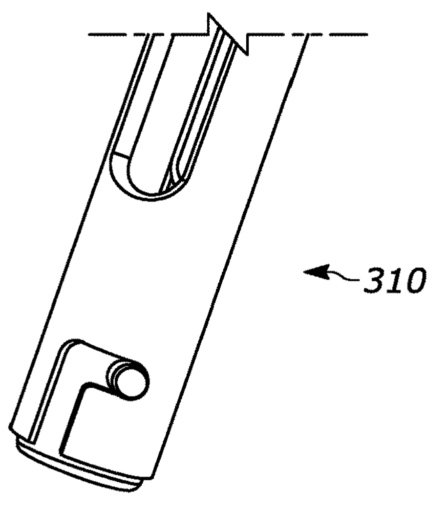
FIG. 4C shows the injector from FIG. 4A, where the needle shield has been depressed and rotated.
Figure 4D:
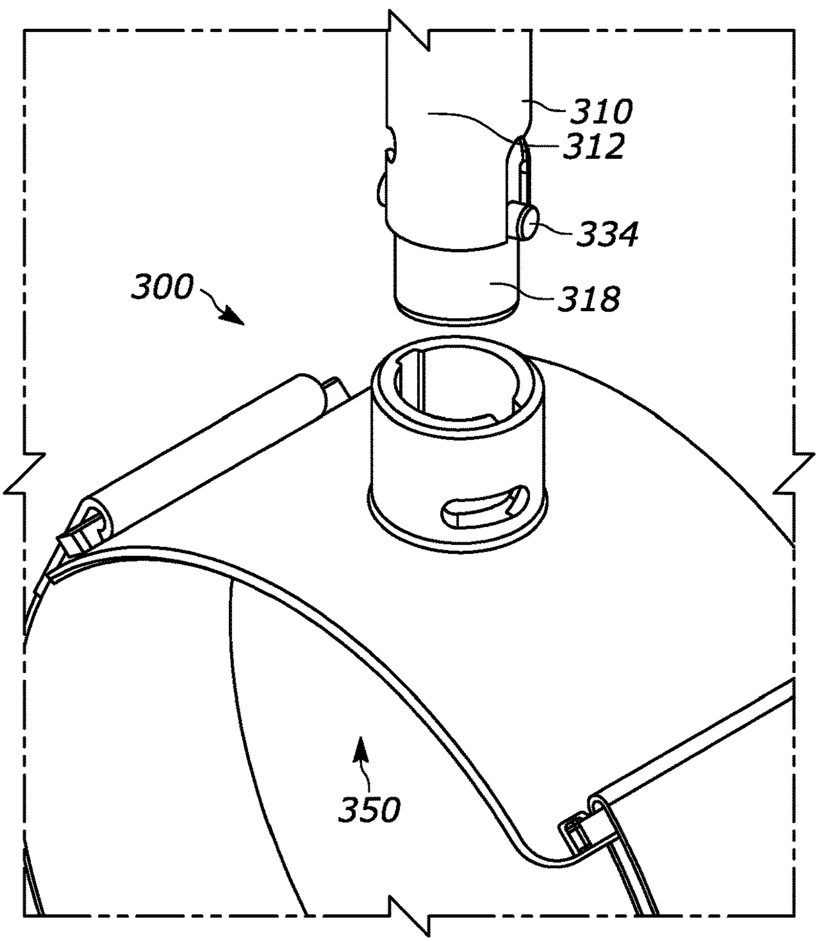
FIG. 4D shows an injector before coupled with an alignment aid according to aspects of the present disclosure.
Figure 4E:
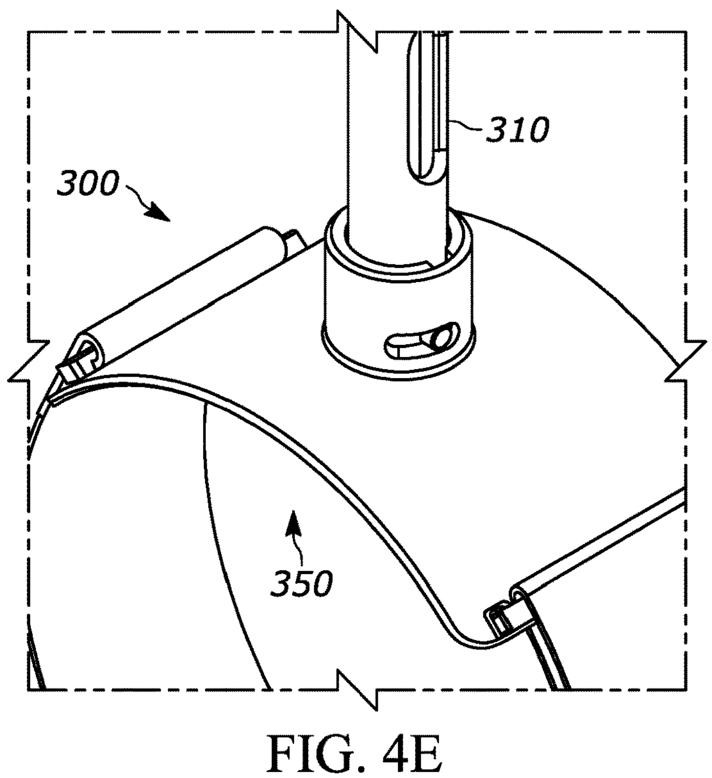
FIG. 4E shows the assembly from FIG. 4D once the injector has been fully inserted but not locked.
Figure 4F:
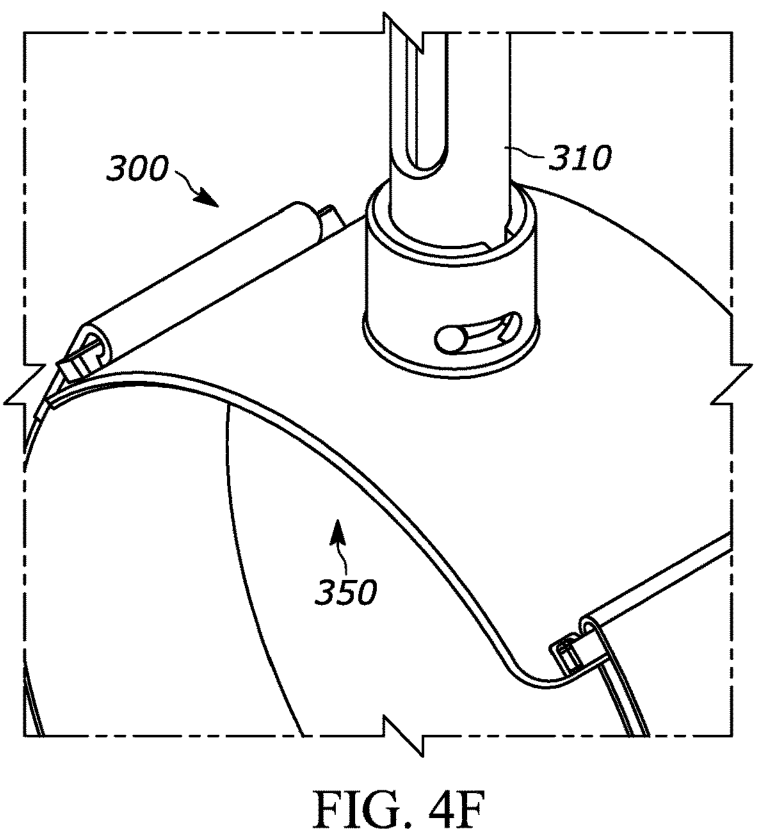
FIG. 4F shows the assembly from FIG. 4D once the injector has been locked (via rotation) with the accessory.

FIGS. 4A-4C show another embodiment of an injector 310 with a needle shield 318 that it is able to be longitudinally locked with respect to the injector housing 312 (FIG. 4C) when the injector 310 is locked with the accessory 350 via rotation. Rotation of the needle shield 318 with respect to the injector housing 318 may also trigger the injection sequence. FIGS. 4D-4G show the injector 310 during stages of coupling with the accessory 350. FIG. 4D shows accessory 350 once it has been coupled with the patient such that the collar portion is aligned with the desired injection site, but before the injector 310 has been inserted into the body 360. FIG. 4E shows the assembly 300 once the injector 310 has been fully inserted but not locked. The longitudinal movement of the injector 310 may depress the needle shield 318. FIG. 4F shows the assembly 300 once the injector 310 has been locked (via rotation) with the accessory 350 so the needle shield 318 rotates with respect to the injector housing 318 and thereby triggers the injection sequence. Also, at this point, the user may be able to release/let go of the injector without necessarily affecting the injection efficacy and/or repeatability.

Figure 5A:
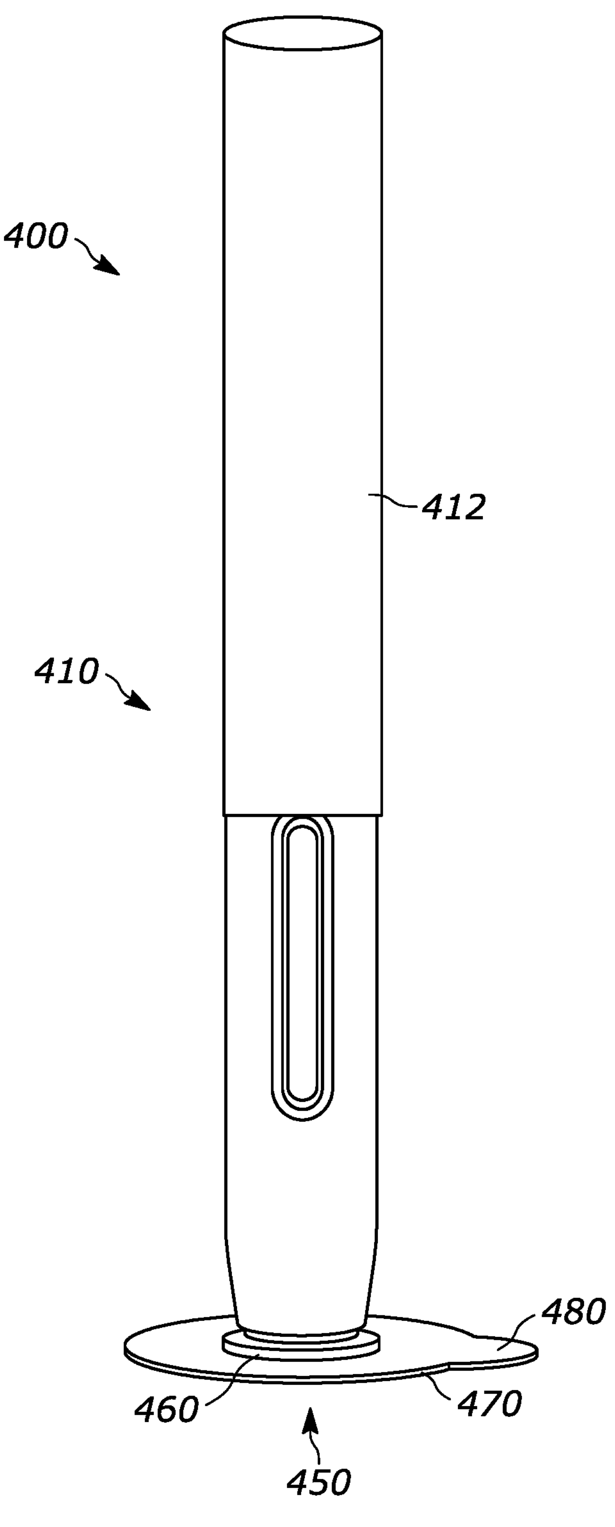
FIG. 5A is a front view of an exemplary drug delivery device assembly according to aspects of the present disclosure, including an injector and an accessory having an alignment aid.
Figure 5B:
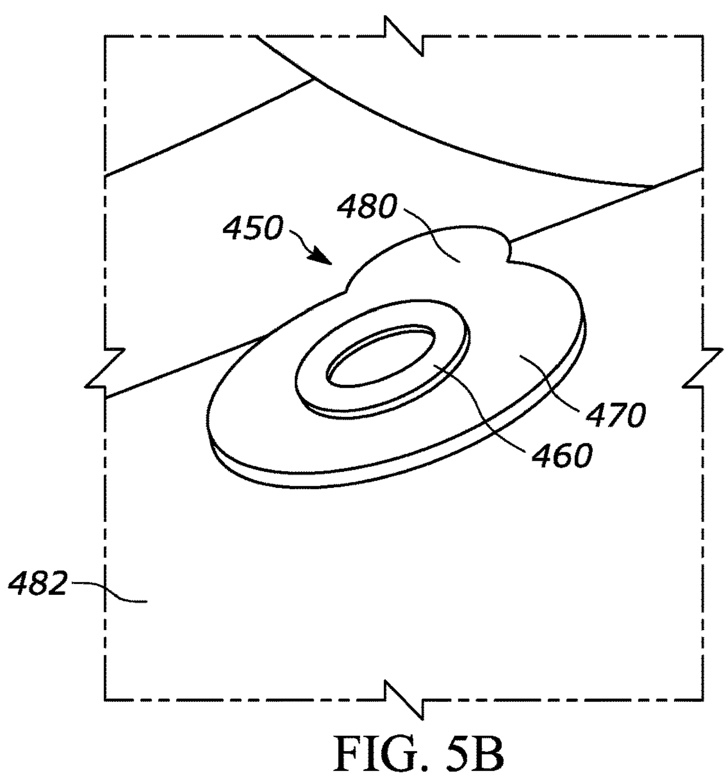
FIG. 5B is a perspective view of the alignment aid shown in FIG. 5A.
Figure 5C:
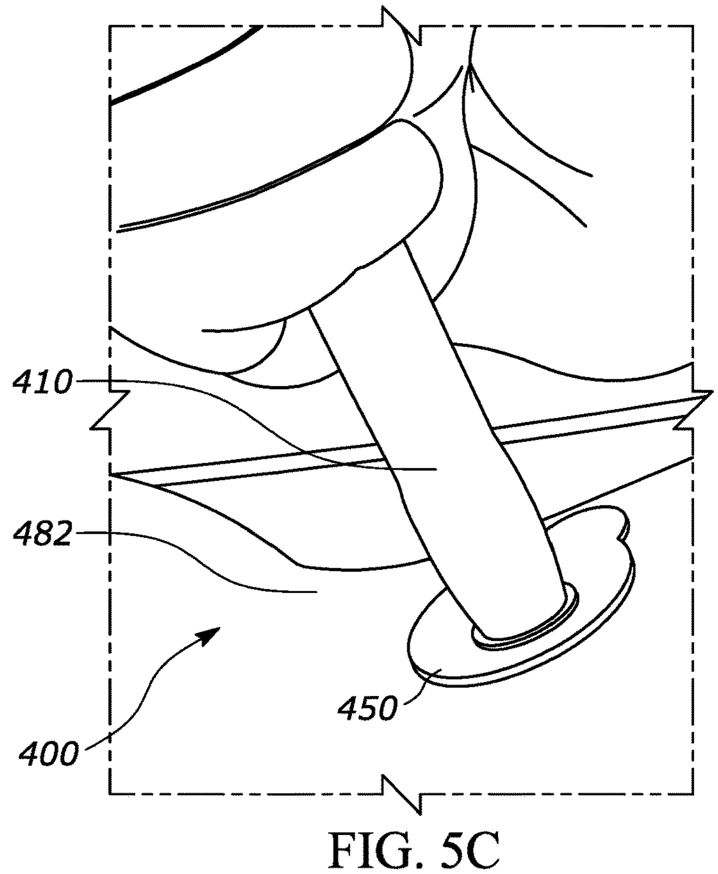
FIG. 5C is a perspective view of the alignment aid and injector shown in FIG. 5A.

FIGS. 5A-5C shows a drug delivery device assembly 400, including an injector 410 and an accessory 450 according to aspects of the present disclosure. The accessory 450 includes an accessory body 460 configured to be selectively coupled with the injector housing 412, an alignment aid 470 configured to aid alignment of the accessory body 460 with respect to the patient's skin at the injection site.

The accessory body 460 may include a generally cylindrical ring 460 configured to receive a portion of the injector housing 412. The cylindrical ring 460 may be generally rigid and may have a diameter sufficiently large enough to receive the needle shield 418 or another component of the injector 410 such as a distal portion of the injector housing 412, thereby aligning the injector 410 with the desired injection site. The accessory 450 also includes an alignment aid 470 configured to aid alignment of the accessory body 460 with respect to the patient's skin at the injection site. For example, the accessory 450 shown in FIGS. 5A-5C includes an adhesive patch configured to be selectively adhered to the skin. The alignment aid 470 may have a relatively wide diameter that contacts the user's skin adjacent to the intended injection, such that the contact forces acting on the users skin may be more spread out, the user's skin may be less likely to buckle or fold during contact, and/or it may be easier for the user to hold the drug delivery device in the desired orientation (perpendicular to the injection site). As a more specific example, the diameter of the alignment aid 470 may be 1 to 1.5 times larger than the diameter of the injector 410. Alternatively, the diameter of the alignment aid 470 may be 1.5 to 2 times larger than the diameter of the injector 410, 1.5 to 3 times larger than the diameter of the injector 410, 1.5 to 4 times larger than the diameter of the injector 410, or any other suitable size. The size of the alignment aid 470 may also serve another function, such as helping the user properly align the injector in a direction such that the needle is generally perpendicular to the patient's skin at the injection site.

Figure 6:
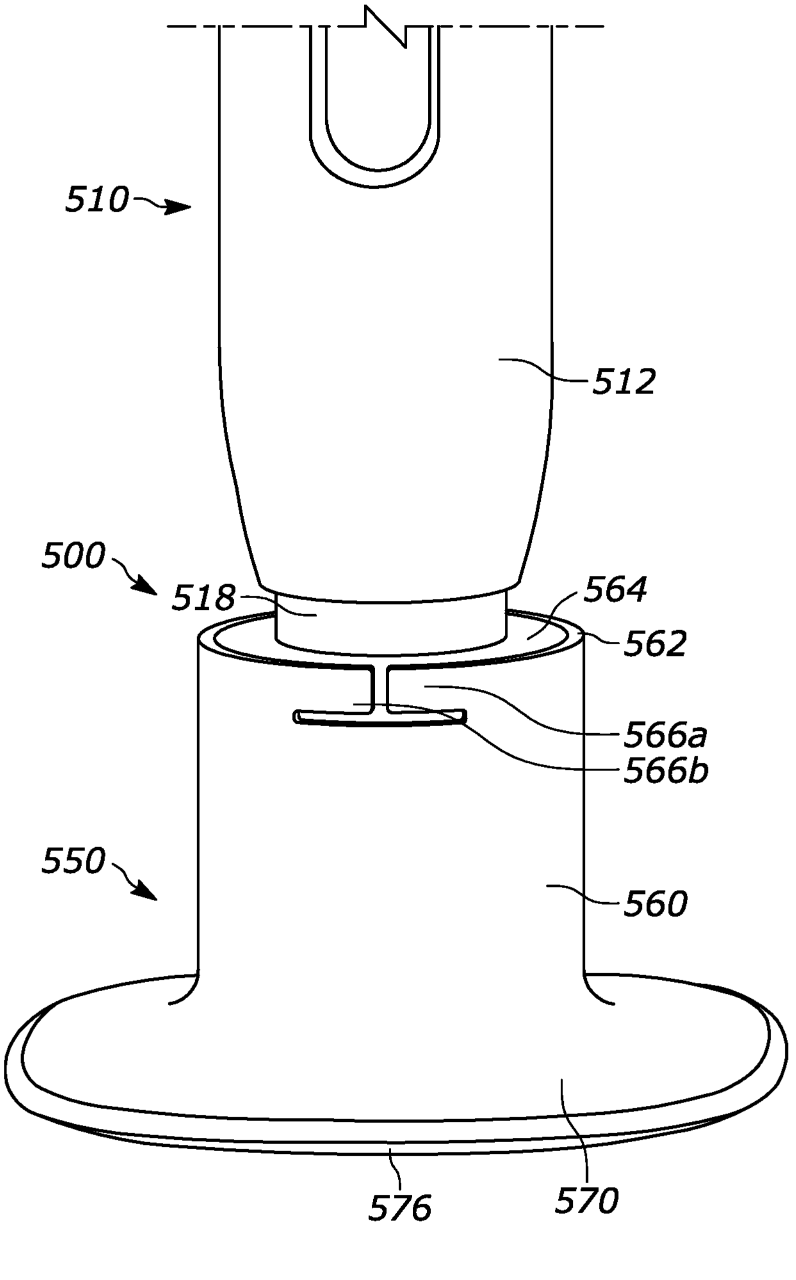
FIG. 6 is a perspective view of an exemplary drug delivery device assembly according to aspects of the present disclosure, including an injector and an accessory having an alignment aid, wherein the accessory and the alignment aid are in a disconnected state.

FIG. 6 shows a drug delivery device assembly 500, including an injector 510 and an accessory 550 according to aspects of the present disclosure. The accessory 550 includes an accessory body 560 configured to be selectively coupled with the injector housing 512, an alignment aid 570 configured to aid alignment of the accessory body 560 with respect to the patient's skin at the injection site. The accessory 550 may also aid the user in activating the injector 510 by providing a wider, more stable surface against which the injector needle shield 518 can be depressed and/or retracted into the injector housing 512.

The accessory body 560 may include a generally cylindrical sleeve 562 defining a generally cylindrical opening 564 configured to receive a portion of the injector housing 512. The accessory 550 may also include at least one coupling feature for releasably or selectively connecting the accessory 550 and the injector 510. For example, the accessory body 560 shown in FIG. 6 includes at least one coupling feature such as a pair of coupling arms 566*a*, 566*b* that form a friction-based fit and/or a press-fit between the accessory 550 and the injector 510. As a more specific example, the coupling arms 566*a*, 566*b* may be spring arms that apply a radially-inward force onto the outer surface of the injector housing 512 when the injector is inserted into the accessory body 560, thereby selectively coupling the accessory 550 and the injector 510. As an even more specific example, the arms 566*a*, 566*b* may have a size and shape (such as a particular thickness) such that they flex radially-outward when the injector is inserted into the accessory body 560, thereby causing the radially-inward force.

As mentioned above, the accessory 550 includes an alignment aid 570 configured to aid alignment of the accessory body 560 with respect to the patient's skin at the injection site. For example, the alignment aid 570 shown in FIG. 6 has a relatively wide contact surface 576 that contacts the users skin adjacent to the intended injection. The relatively wide contact surface 576 may provide the user with a wider surface (i.e., wider than the distal portion of the injector 500) for contacting the users skin, such that the contact forces acting on the users skin may be more spread out, the user's skin may be less likely to buckle or fold during contact, and/or it may be easier for the user to hold the drug delivery device in the desired orientation (perpendicular to the injection site). As a more specific example, the length and width of the contact surface 576 are each approximately 3 to 5 times larger than the diameter of the injector 510. Alternatively, the length and width of the contact surface 576 are each approximately 2 to 6 times larger than the diameter of the injector, 2 to 8 times larger than the diameter of the injector, 2 to 10 times larger than the diameter of the injector, or any other suitable size. The size of the contact surface 576 may also serve another function, such as helping the user properly align the injector in a direction such that the needle is generally perpendicular to the patient's skin at the injection site. As a more specific example, some users may find it easier to align a larger contact surface (e.g., the contact surface 576) with the injection site because it is easier to see and/or feel when the contact surface 576 is parallel with and/or pressed flat against the skin. As another example, the contact surface 576 may also make the skin a more evenly contoured shape in the area of the injection site, thereby causing a more predictable and/or repeatable injection experience.

After the injection is complete, the injector needle shield 518 may extend in a distal (downward in FIG. 6) direction, along the longitudinal axis of the injector 510. This movement may urge or promote relative movement between the injector 510 and the accessory 550, thereby facilitating disconnection between the respective components 510, 550. For example, the movement of the needle shield 518 in the distal direction may urge the accessory away from the housing 512 (or vice versa), thereby potentially overcoming the frictional forces provided by the arms 566*a*, 566*b*. In other words, the force urging the needle shield 518 in the distal direction (likely from a spring force from an internal component inside the injector) may be sufficient to partially or completely overcome the radially-inward force from the arms 566*a*, 566*b* against the housing 512, thereby facilitating disconnection between the respective components 510, 550.

Figure 7A:
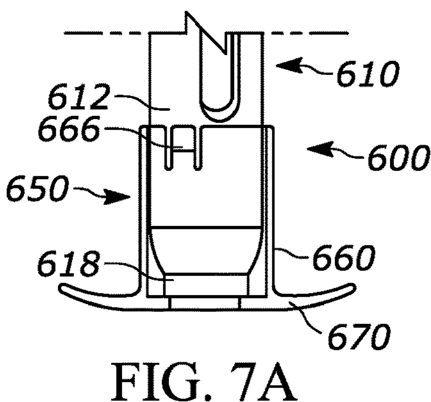
FIG. 7A is a perspective view of an exemplary drug delivery device assembly according to aspects of the present disclosure, including an injector and an accessory having an alignment aid, wherein the accessory and the alignment aid are in a connected, pre-injection state and wherein the alignment aid is partially transparent for illustrative purposes.
Figure 7B:
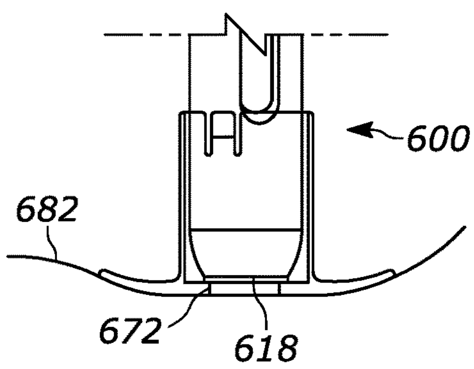
FIG. 7B is a perspective view of the injector and the alignment aid shown in FIG. 7A, wherein the accessory and the alignment aid are in a connected, injection state and wherein the alignment aid is partially transparent for illustrative purposes.
Figure 7C:
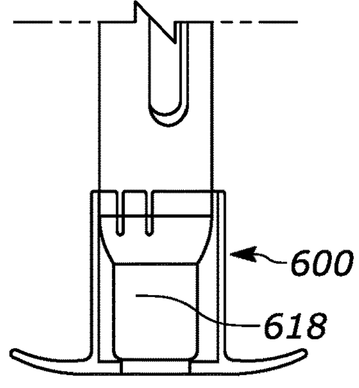
FIG. 7C is a perspective view of the injector and the alignment aid shown in FIG. 7A, wherein the accessory and the alignment aid are in a connected, post-injection state and wherein the alignment aid is partially transparent for illustrative purposes.

FIGS. 7A-7C show a drug delivery device assembly 600, including an injector 610 and an accessory 650 according to aspects of the present disclosure. FIG. 7A shows the assembly with the injector and accessory in a connected, pre-injection state and wherein the alignment aid is partially transparent for illustrative purposes. FIG. 7B shows the assembly with the injector and accessory connected, during an injection (e.g., injection state) where the assembly 600 is abutting/engaged with a patient's skin 682 at a desired injection site. During the injection, the needle shield 618 abuts a bottom surface of the accessory 650, thereby promoting relative movement between the needle shield and the injector housing 612 such as to retract the needle shield 618 into the housing 612 while also permitting a drug delivery member such as a needle to extend through a bottom opening 672 of the accessory. FIG. 7C shows the assembly with the injector and accessory in a connected, post-injection state. The accessory 650 includes an accessory body 660 configured to be selectively coupled with the injector housing 612, an alignment aid 670 configured to aid alignment of the accessory body 660 with respect to the patient's skin at the injection site. The accessory 650 may also aid the user in activating the injector 610 by providing a wider, more stable surface against which the injector needle shield 618 can be depressed and/or retracted into the injector housing 612.

The accessory 650 includes a coupling feature, such as a single coupling arm 666 that operates similarly to the pair of coupling arms 566 shown in FIG. 6.

Figure 8A:
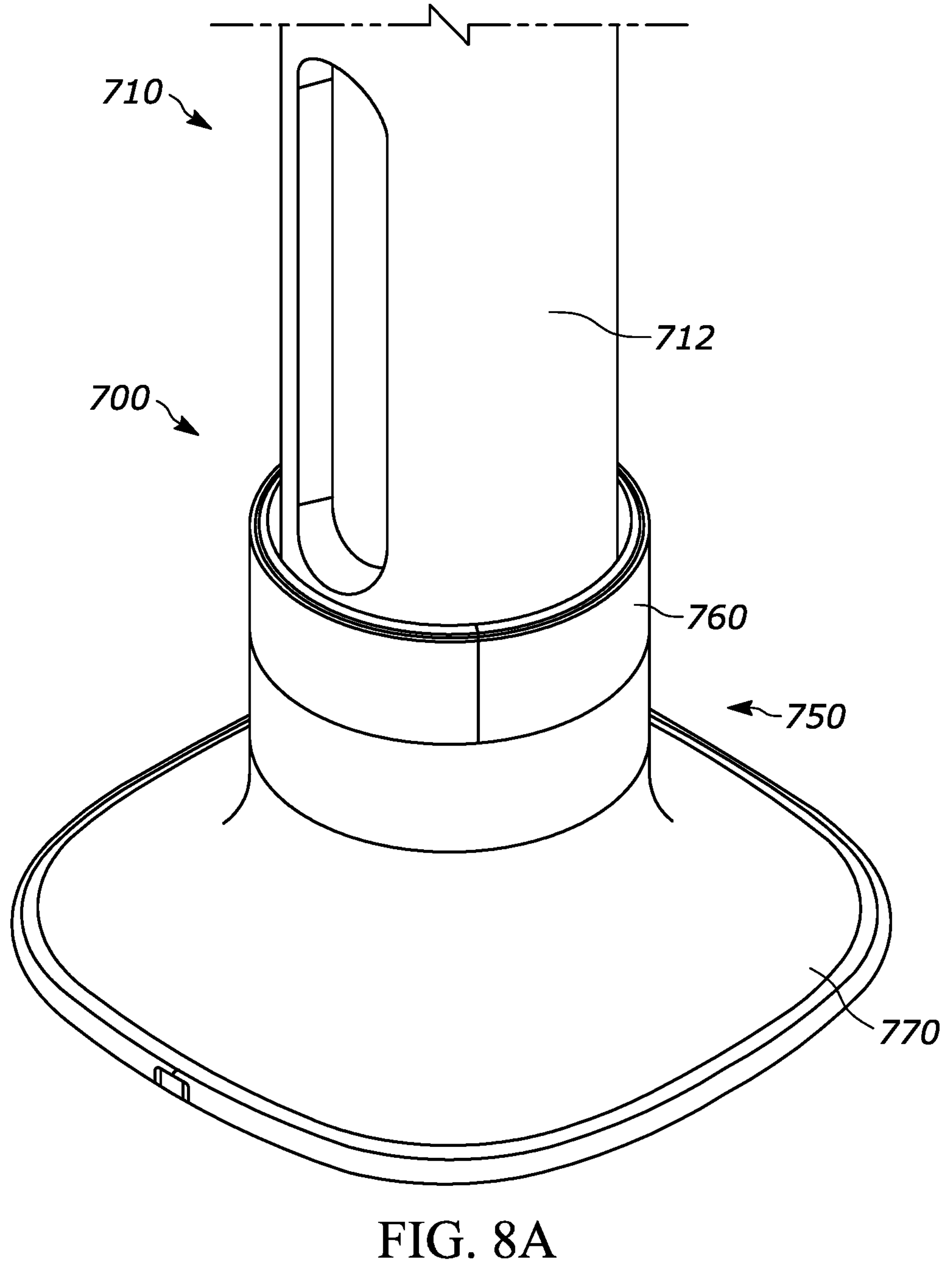
FIG. 8A is a perspective view of an exemplary drug delivery device assembly according to aspects of the present disclosure, including an injector and an accessory having an alignment aid, wherein the accessory and the alignment aid are in a connected state.
Figure 8B:
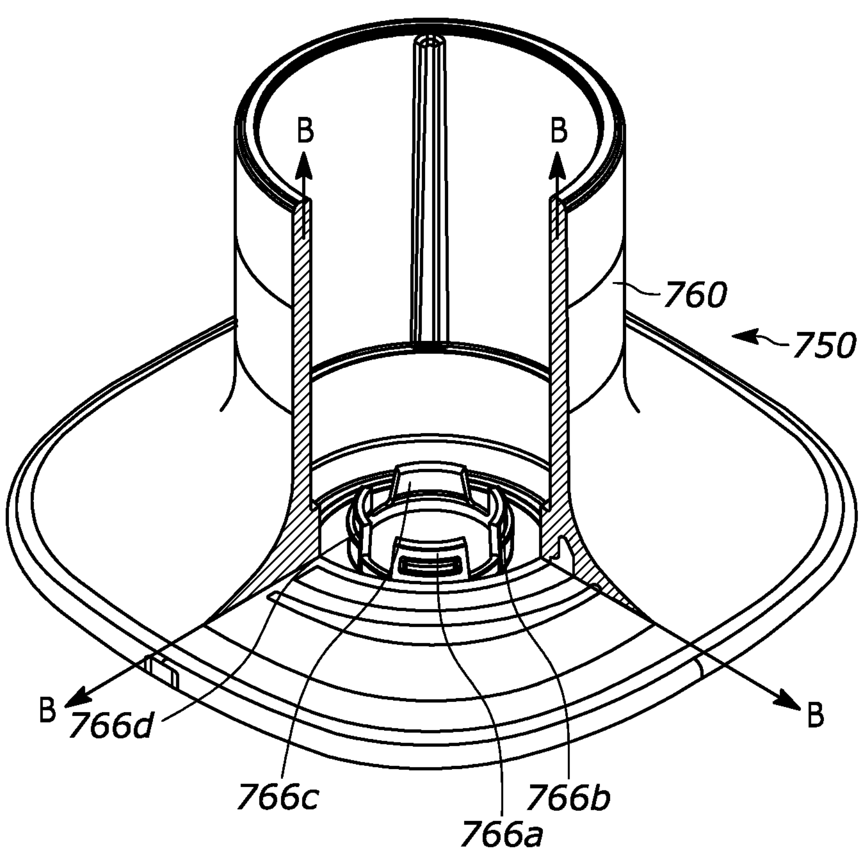
FIG. 8B is a perspective view of the alignment aid shown in FIG. 8A, wherein a portion of the alignment aid is cut away for illustrative purposes, along lines B-B.
Figure 8C:
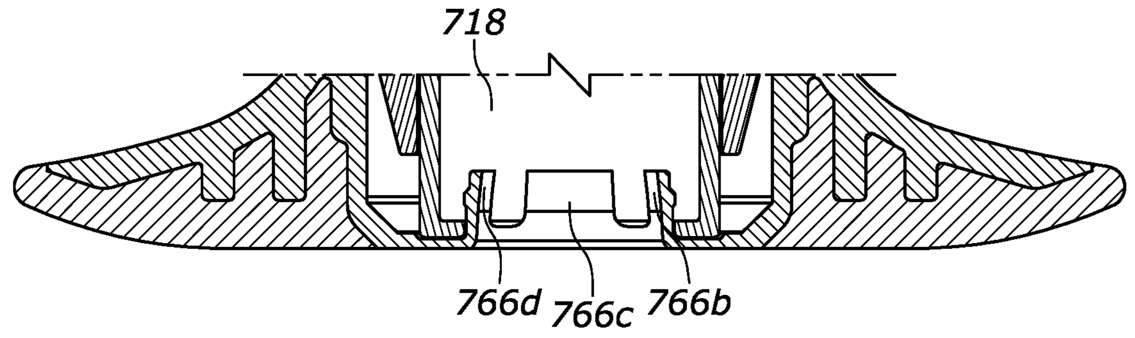
FIG. 8C is a cross-sectional view of a distal portion of the injector and an accessory shown in FIG. 8A, wherein the accessory and the alignment aid are in a connected, pre-injection state.

FIGS. 8A-8C show a drug delivery device assembly 700, including an injector 710 and an accessory 750 according to aspects of the present disclosure. The accessory 750 includes an accessory body 760 configured to be selectively coupled with the injector housing 712, an alignment aid 770 configured to aid alignment of the accessory body 760 with respect to the patient's skin at the injection site. The accessory 750 may also aid the user in activating the injector 710 by providing a wider, more stable surface against which the injector needle shield can be depressed and/or retracted into the injector housing 712.

The accessory 750 may also include at least one coupling feature for releasably or selectively connecting the accessory 750 and the injector 710. For example, the accessory body 760 shown in FIGS. 8A-8C includes at least one coupling feature such as coupling flanges 766 that form a friction-based fit and/or a press-fit between the accessory 750 and the injector 710. As a more specific example, the accessory 750 may include four coupling flanges 766*a*, 766*b*, 766*c*, 766*d* that are each configured to abut and/or engage with the needle shield 718. As a more specific example, the coupling flanges 766*a*, 766*b*, 766*c*, 766*d* may be spring arms that apply a radially-outward force onto the inner surface of the needle shield 718 when the injector is inserted into the accessory body 760, thereby selectively coupling the accessory 750 and the injector 710. As an even more specific example, the coupling flanges 766*a*, 766*b*, 766*c*, 766*d* may have a size and shape such as to permit the flanges to flex radially-inward when the injector is inserted into the accessory body 760 to permit ridges on the flanges to move past the inner surface of the needle shield.

The syringe barrel may have a length of 45 to 85 mm, 60 to 65 mm, or another suitable length. The length of the syringe barrel is the length between the rear end to the outlet to which the needle is attached (but not including the needle, if present).

The syringe barrel may have an internal diameter of 4 to 6.5 mm. If the syringe has a nominal maximum fill volume of 1 ml, the internal diameter of the syringe barrel may be 5.5 to 6.5 mm. If the syringe has a nominal maximum fill volume of 0.5 ml, the internal diameter of the syringe barrel may be 4 to 5 mm.

The wall of the syringe barrel may have a thickness of at least 1 mm; about 1 to 3 mm; about 1.5 to 3 mm; or about 2.4 to 2.8 mm. Due to the thickness of the wall, the sterilizing gas is restricted or prevented from entering interior of the syringe, thereby minimizing or preventing contact with the liquid formulation contained within the prefilled syringe.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RAN KL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-$\alpha 4\beta 7$ mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNF$\alpha$ monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-$\alpha$4integrin mAb); Valortim® (MDX-1303, anti-*B. anthracis* protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2R$\alpha$ mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNF$\alpha$ mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-$\alpha 5\beta 1$ integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFN$\alpha$ mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2R$\alpha$ mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCG8 mAb (MDX-1307); anti-mesothelin dsFv-PE38 conjugate (CAT-5001); anti-PD1mAb (MDX-1106 (ONO-4538)); anti-PDGFR$\alpha$ antibody (IMC-3G3); anti-TGF$\beta$ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TI MP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) molecules such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl) ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™ or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a KRAS$^{G12C}$ small molecule inhibitor, or another product containing a KRAS$^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device assembly comprising:

an injector housing having a body with a proximal end, a distal end, and a longitudinal axis extending between the proximal end and the distal end;

a needle assembly at least partially disposed within the body, the needle assembly comprising a syringe barrel containing a medicament and a needle or a cannula;

a drive assembly at least partially disposed within the body and operably coupled with the needle assembly to urge the medicament through the needle or cannula during an injection sequence, wherein the needle or cannula is configured to pierce a patient's skin at an injection site; and an alignment accessory, including:

an accessory body configured to be selectively coupled with the injector housing; and an alignment aid configured to aid alignment of the accessory body with respect to the patient's skin at the injection site, wherein the alignment aid includes a coupling portion configured to selectively engage a needle shield of the injector.

2. The drug delivery device assembly as in claim 1, wherein the alignment aid is configured to aid alignment of the accessory body with respect to the patient's skin at the injection site by (a) conveying to a user information regarding a position of the accessory body with respect to the patient's skin at the injection site, or (b) maintaining a position of the accessory body with respect to the patient's skin at the injection site.

3. The drug delivery device assembly as in claim 1, wherein the alignment aid includes (a) a first sensor, (b) a first sensor and a second sensor, or (c) a first sensor, a second sensor, a third sensor, and a fourth sensor, each included sensor configured to detect a position of the accessory body with respect to the patient's skin at the injection site.

4. The drug delivery device assembly as in claim 3, wherein the alignment aid includes (c) the first sensor, the second sensor, the third sensor, and the fourth sensor, and wherein the first, second, third, and fourth sensors are generally equally spaced around a circular path along the accessory body.

5. The drug delivery device assembly as in claim 3, wherein the alignment aid includes (c) the first sensor, the second sensor, the third sensor, and the fourth sensor, and wherein the alignment accessory further includes four indicator lights respectively, operatively coupled with the four sensors.

6. The drug delivery device assembly as in claim 1, wherein the alignment aid includes a contoured portion configured to generally fit the contour of a patient's injection site.

7. The drug delivery device assembly as in claim 1, wherein the alignment aid includes a securing portion configured to selectively secure the alignment accessory with the patient.

8. The drug delivery device assembly as in claim 7, wherein the securing portion includes an adjustable strap or an adhesive.

9. The drug delivery device assembly as in claim 1, wherein the accessory body is a ring portion configured to receive a portion of the injector housing.

10. An alignment accessory for a drug delivery device, comprising:

an accessory body configured to be selectively coupled with an injector; and an alignment aid configured to aid alignment of the accessory body with respect to a patient's skin at an injection site, wherein the alignment aid includes a coupling portion configured to selectively engage a needle shield of the injector.

11. The alignment accessory as in claim 10, wherein the alignment aid is configured to aid alignment of the accessory body with respect to the patient's skin at the injection site by (a) conveying to a user information regarding a position of the accessory body with respect to the patient's skin at the injection site, or (b) maintaining a position of the accessory body with respect to the patient's skin at the injection site.

12. The alignment accessory as in claim 10, wherein the alignment aid includes (a) a first sensor, (b) a first sensor and a second sensor, or (c) a first sensor, a second sensor, a third sensor, and a fourth sensor, each included sensor configured to detect a position of the accessory body with respect to the patient's skin at the injection site.

13. The alignment accessory as in claim 12, wherein the alignment aid includes (c) the first sensor, the second sensor, the third sensor, and the fourth sensor, and wherein the first, second, third, and fourth sensors are generally equally spaced around a circular path along the accessory body.

14. The alignment accessory as in claim 12, wherein the alignment aid includes (c) the first sensor, the second sensor, the third sensor, and the fourth sensor, and the alignment accessory further includes four indicator lights respectively, operatively coupled with the four sensors.

15. The alignment accessory as in claim 10, wherein the alignment aid includes a contoured portion configured to generally fit the contour of a patient's injection site.

16. The alignment accessory as in claim 10, wherein the alignment aid includes a securing portion configured to selectively secure the alignment accessory with the patient.

17. The alignment accessory as in claim 16, wherein the securing portion includes an adjustable strap or an adhesive.

18. The alignment accessory as in claim 10, wherein the accessory body is a ring portion configured to receive a portion of the injector housing.

* * * * *